(12) United States Patent
Albert et al.

(10) Patent No.: US 7,049,429 B1
(45) Date of Patent: May 23, 2006

(54) MUTATIONS OF THE 5' REGION OF THE HUMAN 5-HT1A GENE

(75) Inventors: Paul Albert, Ottawa (CA); Sylvie Lemonde, Cantley (CA)

(73) Assignee: University of Ottawa, Ottawa (CA)

( * ) Notice: Subject to any disclaimer, the term of this patent is extended or adjusted under 35 U.S.C. 154(b) by 0 days.

(21) Appl. No.: 09/430,412

(22) Filed: Oct. 29, 1999

Related U.S. Application Data

(60) Provisional application No. 60/106,375, filed on Oct. 30, 1998.

(51) Int. Cl.
*C12N 15/11* (2006.01)

(52) U.S. Cl. ..................... 536/24.1; 536/23.1
(58) Field of Classification Search .............. 536/24.1, 536/23.1; 935/6, 10, 8
See application file for complete search history.

(56) References Cited

OTHER PUBLICATIONS

LeClerc et al., Nature 297: 596-597 (1982).*
"The Serotonin 1a Receptor Gene Contains a TATA-Less Promoter That Responds to MAZ and Sp1" by Parks and Shenk, The Journal of Biological Chemistry, vol. 271, No. 8, Feb. 1996, pp. 4417-4430.

* cited by examiner

*Primary Examiner*—Robert C. Hayes
(74) *Attorney, Agent, or Firm*—Sheridan Ross, P.C.

(57) ABSTRACT

Clinical response to antidepressant compounds correlates with a selective down-regulation of presynaptic 5-HT1A receptors in serotonergic raphe neurons. Thus regulation of the 5-HT1A receptor gene could play a crucial role in the treatment or etiology of major depression. The promoter and repressor activities of the human 5-HT1A receptor gene have been examined. The analysis of the 5'-flanking regions of the 5-HT1A receptor gene has revealed a segment located between about −3438 and about −393 bp upstream from the initiator ATG that mediates cell-specific repression of the gene that is greater in cells that do not express the 5-HT1A receptor. The sequence of part of this region in patients with major depression were examined and a polymorphic C-G change located at −1017 bp was identified, which is associated with major depression. Thus, this sequence can be used as a genetic marker for major depression and related mental illnesses. A protein that binds to the DNA at the −1017 locus has been identified. Any such proteins that bind to the DNA at this region are important targets for the development of therapeutic compounds for the treatment of major depression and related mental illness that involve the serotonin system. In addition the promoter region from about −393 to the initiator ATG displays glucocorticoid-mediated repression.

6 Claims, 9 Drawing Sheets

Human 5-HT1A promoter

-3438 ATCATCATCAATAATATATCCGTTATAAAGCTTGCTTTCTTTAGTTAACTTTAGAGGCCCTTGAAGAATAAGAGCTCATCTCTT
-3358 TACAGGAGAGCTTTGTTTGCAGCATTTACTTAAGAAATATTTGGTATTCTGTATCTTAAGAGTTAACATAGAAGAATTG
-3278 GCTAAGTGAAATGAATGAAAACGAATATCATCTGCATATATCATTTATTATATATCACAGTATTATTAGTTTTAAAAG
-3198 TTAAACATAAATATCTATTATGYCATTGSACGAYTAGGYSAACCTARTCRGTGCTGCGAATACTTTCGATACTTCTGTTT
-3118 CCCCTCCTAGTATTCATAAGTGTGCCTTTGAAAACGTTTTAAATTGTAAGAAATAAAATGTTTGATATATTATGTATATTA
-3038 TTACTAAGAAAAACTTGAATTACTTTGGATTTTGAAATTCTACATCATAGCATATTGAAGCAAGAAT
-2958 AACAAATGCTATACCTCAGGAATATTAATTCCAGATTTTAACTTTCTTGATGAGAAAAATAAATTTGTC
-2878 AGTTATTAAACTATTGGATCCAACAGATGAAAGCAGAATTCTAACATATTTATTGTGATTTACATA
-2798 TTTACATGTGTTGTTTGACACAATTCTTAATTATGTTCTTGATATGCATATATATTGCTTCTTAAATTTTAAGTTTCCTTT
-2718 ATTTTACTTTGTTTATAGTCTCAACTATAATTTCAAAGTTTAATTTAGATAATTCAGCCTTTTAAATATTTCCATTA
-2638 TAATTTTGTGACCTCTAACTCTATTTAACTGTAAATATAGTTCTGTATTTGTGAAGAGACTTTAGAAGTGAAATAGA
-2558 TACCCTTCACAAATCTTAAAAGACTTCTTCAGAGTCTGTAAACAGCATTACCATGTATACTTATCTCTTTCTTTGCATGCC
-2478 ATGATCATCACAATGCATGCTCATGTGGTGGCATGCTGAATGATTGAGTGGGACTGTGCCAGCTGAACTATAAAAAAAA
-2398 AAAAACAAACAAAACAAACCTTATCCAAACACTGTCCTGTATGTAATGCATTGGCCCAACTGGATTCTTTTTGATGCTTTGG
-2318 TGATTGCTCTTTGTTGGGCTTGAGAATTCAGAGCTATGAAATTCAGAGCTCAGATTTGAACACAATATTAAGATTAT
-2238 TGCAATCTGTAGTGAATCTGTTCATGTTCATCCAGTGTCAACTGCTTTTGAGATTGCATTCCTTTCACCTCAGGCATGCAA

FIGURE 1a

```
-2158 TCAGGATGTATAAGTGAAATGTTGTGTGGTATGTTACTGTAGTTGCTTAGAAGTCCATTCTTTACCAATGCTCAAATGT
-2078 GATTAAATTTGTTTCTTGTTAAAGGAAACAGCTTAGAACAAACCCTGTAAGTATCTTTATTTCAGTGATTTAACATTT
-1998 CCAAATGTTAAATCATTTGGAAAATGCAATACTATTCGTTTCTCCAACAAAAGGTAAATTTATGTCAGTTCCAAAGTTCA
-1918 GGTTTATGACAGCACATAAACCAACACAGTGAAAGTGTTAGCCTAGCTTTATTAAAATGCATTCCCAGTTAGAACTTGTG
-1838 AAATGACAGATACTTCAGGCTTTCGAAGGAAGCTAAAACATATAATAAGGTTCAGAGCAAAAGAGGGC
-1758 ACTAAAATAAATTTTAAAGAAAATAGGAAGGAGACAAAACTCAATACTACCTTGTCTTTTAATAACTGTCTTCCTCTTT
-1678 CTAAAAGTTGTTGTATTTCCTCAATACTTGCTTCATTTCTGGCATAAGGGTTTCCAGATGCACTCTAAAACATTTGCCA
-1598 GAAGGTGGCGAACATAAAACCTCATTGCTTAGAACTGTCCCCAGGTGCTGAACCCAGTTTCTGAGATTAAGAGAGGCTAGC
-1518 CGGCTAGCGAACCGGGATTCCACCAAGTTCCCCCAGAGGTTTGCAGGCTCTGGTAAGAAGTGCAAAAGGCCATGTGAAA
-1438 TGCCAGGCTTCACTTAGAACACATATGCAAAATATTTCCATCCCTGAATTTACTAGCCACAAAGCTATGGAAGTGGCAG
-1358 TGTCACTGAATTACAAGTGTAGTAGTGATGGAAAAGTGTGTGTTTAGAATATATATCACACTGAGTTTTGTTCTT
-1278 CATTTCGAGATGCAGTTGTTTACCTCTCCTTGTCCTTTGACACGTCCTTTATAATTTCGTTCTCTCCCGGTTCCCCAACG
-1198 TTAAAAAAAAGTCACAGGCAATATTCTCCCTGAGGAGTAAGGCTGGACTGTTAGATGATAACGGAGGTACCGTTTTGT
-1118 TGTTGTTGTCGTCGGTTGTTGTTCGTTGTTTTTGGAGACGGAGTCTCGCTCTGTCGCCCAGGCTGGAGTGCAATGGCGCGAGA
-1038 ACGGAGGTAGCTTTTTAAAAACGAAGACACACTCGGTCTTCTTCTTCCATCAATTAGCAATAATTGGGAGACTGACCCAGGAC
-958  TGTTCACCTTCCATTCAGGCTCCATTCAGGCTCCCTATGCTTCCTTTTCTCATTCTCCTATTGCCACTCTGGGATGCTGACACGATTTAAG
-878  AAATTTGGCAGATAATATGAGGCAAGGAGTAGTTGGAATTCCCTCCCCCAAGTTTTTCCAACCCCAGTTTTGCTGGGTTGG
-798  AGGCGGAGTTTATTTGTTACAACCTTGGTCTGACCGGCAGGATCTGGTGTGTAAGTGAGTTCTGAGTCTCTGTTGACA
-718  AAAAGAGACTCGAATGCAAAGACGCTGAGCTAGAGGGAGAGGAGGGCGGGACCCAGAGGAAAGAGGCCACTCCTCGGGGT
```

FIGURE 1b

-638 TGGGGAAGTATTAGGAGGGAGGGTTAGAGTGGGAGGGAAGGAGCCTGGCTTTCGAAGCGACTCACAGAGGGATAAATAA

-558 AGGGAAGTGAGGAGGAAGAGGAGACTGAAAGGGACGCAGGTGGGGAGAAGGGACGAAAGAGGCAGAAGAGAGAGAA

-478 GAGAGGAGGAGAGAGGGGAGAGAGGGAAGGAGAAATAGGAGAGAGGTCACAGAGTGACCGTGGAGGATGGGGCT

-398 TCTCG

FIGURE 1c

| RN46A NUCLEAR EXTRACT | − | + | + | + |
| 100X COLD SPECIFIC OLIGO | − | − | + | − |
| 100X COLD NON-SPECIFIC OLIGO | − | − | − | + |

SEQUENCE LISTING

<160> NUMBER OF SEQ ID NOS: 7

<210> SEQ ID NO 1
<211> LENGTH: 3045
<212> TYPE: DNA
<213> ORGANISM: human

<400> SEQUENCE: 1

```
atcatcaata atatccgtta taaagcttgc ttttctttag gttaacttta gaggccttga      60
agaataagag ctcatctctt tacaggagct ttggtttgca gcatttactt aagaaatatt     120
tggtattctg tatctttaag agttaaacat agaagaattg gctaagtgaa aatgaatgaa     180
acgcaatatc attctgcata tatcatttat tatatatcac agtattatta gttttaaaag     240
ttaaacataa atatctatta tgycattgsa cgaytaggys aacctartcr gtgctgcgaa     300
tactttcgat acttctgttt ccctcctagt attcataagt gtgcctttga aaacgtttta     360
aattgtaaga aataaaatgt ttgatatatt atgtatatta ttactaagaa aaaacttgaa     420
ttactttgga ttttgaaaaa ctttgataaa ttctacatca tagcatattg aagcaagaat     480
aacaaatgct atacctcagg aatattaatt ccagatttta cagcatttta actttcttga     540
tgagaaaaaa taaatttgtc agttattaaa ctatttggat ccaacagatg aaagcagaat     600
tctaactaac atatttattg atttatttgt gatttacata tttacatgtg ttgtttgaca     660
caattcttaa ttatgttctt gatatgcata tatttgcttc ttaaatttta agtttccttt     720
attttacttt gtttatagtc tcaactataa tttcaaagtt taattttaga taattcagcc     780
ttttaaatat tttcccatta taatttttgt gacctctaac tctattttaa ctgtaaatat     840
agttctgtat ttgtgaagag actttagaag tggaaataga taccttcaca aatcttaaaa     900
gacttcttca gagtctgtaa acagcattac catgtatact tatctctttc tttgcatgcc     960
atgatcatca caatgcatgg ctcatgtggt ggcatgctga atgattgagt gggactgtgc    1020
cagctgaact ataaaaaaaa aaaacaaaca aaaccttatc caaacacact gtcctgtatt    1080
gtaatgcatt ggcccaactg gattcttttt gatgctttgg tgattgctct tttgtttggg    1140
cttggagaat tcagagctat gaaattcaga gctcagattt gaacacaata ttaagattat    1200
tgcaatctgt agtgaatctg ttcatgttat ccagtgtcaa ctgcttttga gattgcattc    1260
ctttcacctc aggcatgcaa tcaggatgta taagtgaaat gttgtgtggt atgtttactg    1320
tagttgctta gaagtccatt ctttaccaat gctcaaatgt gattaaattt gttttcttgt    1380 taaggaaac agcttagaac aaaccttgt aagtatcttt atttcagtga tttaacattt      1440
ccaaatgtta aatcatttgg aaaatgcaat actattcgtt tctccaacaa aaggtaaatt    1500
```

```
tatgtcagtt ccaaagttca ggttatgaca gcacaaaacc aacacaggtg aaagtgttag    1560
cctagcttta ttaaaatggc attcccagtt agaacttgtg aatgacagat acttcaggct    1620
ttcgaaggaa gctaaaacat ataataggcc tgatatataa ggttcagagc aaaagagggc    1680
actaaaataa attttttaaag aaaataggaa ggagacaaaa ctcaatacta ccttgtcttt    1740
taataactgt cttcctcttt ctaaaagttg ttgtatttcc tcaatacttg cttcatttct    1800
ggcataaggg tttccagatg gcactctaaa acatttgcca gaaggtggcg aacataaaac    1860
ctcattgctt agaactgtcc caggtgctga acccagtttc tgagattaag agaggctagc    1920
cggctagcga accgggattc caccaagttt cccccagagg tttgcaggct ctggtaagaa    1980
gtgcaaaagg ccatgtgaaa tgccaggctt cacttagaac acatatgcaa aatatttcca    2040
tccctgaatt tactagccac aaagctatgg gaagtgcag tgtcactgaa attacaagtg     2100
tagtagtgat ggaaaagtgt gtgtgtgttt agaatatata tcacactgag ttttgttctt    2160
catttcgaga tgcagttgtt tacctctcct tgtcctttga cacgtccttt ataatttcgt    2220
tctctcccgg ttccccaacg ttaaaaaaaa agtcacaggc aatattctcc ctgagggagt    2280
aaggctggac tgttagatga taacggaggt accgttttgt tgttgttgtc gtcgttgttc    2340
gtttgttttt ggagacggag tctcgctctg tcgcccaggc tggagtgcaa tggcgcgaga    2400
acggaggtag cttttttaaaa acgaagacac actcggtctt cttccatcaa ttagcaataa    2460
ttgggagact gacccaggac tgttcacctt cccattcagg ctccctatgc ttccttttct    2520
catctcctat tgccactctg ggatgctgac acgatttaag aatttggcag ataatatgag    2580
gcaaggagta gttggaattc cctcccccaa gttttttccaa ccccagtttt gctgggttgg    2640
aggcggagtt tatttgttac aaccttggtc tgaccggcag gatctggtgt gtgtaagtga    2700
gttctgagtc tctgttgaca aaaagagact cgaatgcaaa gacgctgagc tagagggaga    2760
ggagggcggg gacccagagg aaagaggcac tcctcgggt tggggaagta ttaggagggg     2820
agggttagag tgggagggaa ggagcctggc tttcgaagcg actcacagag ggataaataa    2880
agggaagtga ggaggaagag ggagactgaa agggaaggca ggtggggaga aggggggacga   2940 aagaggcaga agagagagaa gagaggagga gagagggga gagagggaag gaaggaaata     3000
gggagaggag ggtcacagag tgaccgtgga ggatggggct tctcg                    3045
```

<210> SEQ ID NO 2
<211> LENGTH: 24
<212> TYPE: DNA
<213> ORGANISM: human
<220> FEATURE:
<221> NAME/KEY: misc_features
<222> LOCATION: (1)...(24)
<223> OTHER INFORMATION: n=a, c, g, or t

<400> SEQUENCE: 2

```
aacgaagacn nnnnnngtct tctt                                              24
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: sense
     primer

<400> SEQUENCE: 3

```
gtggcgaaca taaaacctca                                                   20
```

```
<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: antisense
      primer

<400> SEQUENCE: 4
ttcttaaatc gtgtcagcat c                                              21

<210> SEQ ID NO 5
<211> LENGTH: 29
<212> TYPE: DNA
<213> ORGANISM: human

<400> SEQUENCE: 5
ttaaaaacga agacacactc ggtcttctt                                      29

<210> SEQ ID NO 6
<211> LENGTH: 29
<212> TYPE: DNA
<213> ORGANISM: human

<400> SEQUENCE: 6
ggaagaagac cgagtgtgtc ttcgttttt                                      29

<210> SEQ ID NO 7
<211> LENGTH: 31
<212> TYPE: DNA
<213> ORGANISM: rat

<400> SEQUENCE: 7
cggcataagc aagcccttat tgcacagagc t                                   31
```

MUTATIONS OF THE 5' REGION OF THE HUMAN 5-HT1A GENE

CROSS-REFERENCE TO RELATED APPLICATIONS

This application claims the benefit of priority under 35 U.S.C. § 119(e) from U.S. Provisional Application Ser. No. 60/106,375, filed Oct. 30, 1998.

FIELD OF INVENTION

The present invention relates to a DNA sequence of the 5' flanking region of the 5-HT1A receptor gene, from about −3438 to about −393, wherein said sequence contains a mutation that results in a reduction of protein-DNA interactions. This invention further relates to proteins, which bind to this region and the use of said proteins to develop therapeutics to treat depression and related illnesses that involve the serotonin system. This invention also relates to a diagnostic or prognostic test for mental illnesses, and other conditions that involve the serotonin system, using the novel DNA sequence as a genetic marker. This invention also relates to a glucocorticoid-responsive element located from about −393 to the ATG initiation codon of the 5-HT1A receptor gene.

BACKGROUND OF THE INVENTION

Serotonin (5-HT), a key neurotransmitter in the central nervous system, is believed to play a role in various cognitive functions such as sleep, pain perception, depression, learning and anxiety (Blier et al., 1990; Jacobs and Azmitia, 1992; Mongeau et al., 1997). Neurons of the raphe nuclei which release serotonin have axons that project widely throughout the brain to innervate a variety of nuclei (Tork, 1990). The activity of the raphe nucleus is controlled in part by inhibitory somatodendritic 5-HT1A autoreceptors. The serotonin 1A (5-HT1A) receptor belongs to the seven-transmembrane G-protein coupled receptor superfamily (Hoyer et al., 1994). Its activation inhibits adenylyl cyclase activity, increases K+ conductance causing a decrease in action potential frequency, and decreases the opening of voltage-dependent calcium channels (Penington and Kelly, 1990; Penington et al., 1993; Zgombick et al., 1989). An important function of 5-HT1A autoreceptors in the raphe nuclei is thus to control the frequency of action potential firing. Increase in action potential frequency leads to serotonin release at the cell body, which activates the 5-HT1A receptor to decrease raphe firing and reduce the release of serotonin, as part of a negative feed-back loop (Albert et al., 1996).

Recent studies have suggested that the level of expression of 5-HT1A autoreceptors may play a role in the treatment and possibly the etiology of major depression (Albert et al., 1996; Blier and de Montigny, 1994; Mongeau et al., 1997). Antidepressant compounds (monoamine oxidase inhibitors, tricyclic reuptake inhibitors, and especially serotonin-selective reuptake inhibitors (SSRIs)) act to enhance serotonin release by inhibiting its elimination. These compounds are effective in the treatment of a variety of mental illnesses including major depression, bipolar depression, generalized anxiety disorder, and obsessive compulsive disorder, but 2–3 weeks of treatment are required before clinical improvement may be observed (Charney et al., 1990). Acute treatment with antidepressants to enhance synaptic serotonin levels leads to inhibition of the firing rate of raphe neurons via activation of 5-HT1A autoreceptors, which prevent enhancement of serotonin release (FIG. 2). Chronic (2 weeks) treatment with serotonin uptake inhibitors (eg. fluoxetine) and selective 5-HT1A partial agonists (eg. buspirone) results in a selective downregulation of presynaptic (eg. raphe) but not postsynaptic 5-HT1A receptors (hypothalamus, cortex, hippocampus) (Fanelli and McMonagle-Strucko, 1992; Welner et al., 1989). Desensitization of the 5-HT1A autoreceptor results in restoration of raphe firing rate and enhanced serotonergic neurotransmission (FIG. 2) that correlates with behaviourial improvement induced by antidepressant treatments.

As longterm regulation of the 5-HT1A receptor is implicated in major depression, we have investigated the promoter of the human 5-HT1A receptor gene to characterize and identify specific loci associated with depression. Changes in gene expression persist for days to weeks, and could underlie the down-regulation of 5-HT1A receptors by antidepressant compounds over the 2-week treatment period.

SUMMARY OF THE INVENTION

The present invention relates to a proximal ubiquitous promoter region flanked by a repressive region containing several elements of interest including the RE-1 element (Schoenherr and Anderson, 1995) and a poly GT dinucleotide repeat also present in the equivalent region of the rat gene. Within the proximal 5'-flanking region of the human 5-HT1A receptor a novel glucocorticoid responsive region that suppresses reporter gene expression has been identified in the present invention. Using PCR and DNA sequence analysis of the 5-HT1A receptor gene from blood samples of depressed patients, we have further identified in the repressor region a polymorphic C-G conversion that is located at −1017 bp upstream of the initiation ATG codon. This sequence polymorphism occurs in 34/43 depressed patients, and 13/43 are homozygous for the polymorphic allele (2 copies). In blood samples from normals, 12/23 are heterozygous for the polymorphism, while 0/23 carry the homozygous form.

The present invention thus relates to a DNA sequence of the 5' flanking region of the 5-HT1A receptor gene, from about −3438 to about −393 (SEQ ID NO:1), wherein said sequence contains a mutation which results in an inhibition of protein-DNA interactions. The partial wild type sequence of the human 5-HT1A receptor gene is deposited in Genbank and has been published by Parks and Shenk (1996). More specifically this invention relates to a AND sequence comprising a polymorphic C-G change at position −1017 (position 2422 of SEQ ID NO:1) of the 5-HT1A receptor gene and to a 31 base pair region flanking the −1017 locus.

This invention further relates to proteins, which bind to this region and the use of said proteins to develop therapeutics to treat depression and related illnesses that involve the serotonin system. More specifically this invention relates to a protein which binds to a 31-bp region surrounding the −1017 bp polymorphism.

This invention also relates to a diagnostic or prognostic test for mental illnesses that involve the serotonin system using the novel DNA sequence of the present invention as a genetic marker. Kits for conducting the tests of the present invention are also included within the scope of this invention.

This invention is also includes a method of identifying novel therapeutics using a DNA sequence containing a mutation in the repressor region of the 5-HT1A receptor gene, wherein said therapeutics will modify the protein-DNA binding, which is reduced in patients suffering from depression and related illnesses.

This invention also includes a glucocorticoid-responsive element located between −393 and the initial ATG codon.

BRIEF DESCRIPTION OF THE DRAWINGS

These and other features of the invention will become more apparent from the following description in which reference is made t the appended drawings wherein:

FIGS. 1a, 1b and 1c shows the promoter region of human 5-HY1A from −3438 to −393 (SEQ ID NO:1). The position of the polymorphism at −1017 is shown by an arrow.

FIG. 5A is the wild type sequence with a C at position −1017. FIG. 5B shows a heterozygous individual for the mutation, with both a C and G at position −1017 bp. FIG. 5C is the homozygous mutant sequence, showing a G at position −1017. The repressive region of the human 5-HT1A promoter was analyzed for length and size variations using blood samples from depressed patients and normals. A 718-bp fragment was amplified by PCR and sequenced within the region of the promoter between −1593 to −876 bp of the initial ATG codon. Shown is DNA sequence analysis in the region of −1017 bp from PCR products of 3 different patients which revealed patients with: the wild-type sequence A (figure shows positions 2411–2433 of SEQ ID NO:1), with a C at position −1017 from the initial ATG codon; sequence heterozygous for the mutation with both a C and a G nucleotide at −1017 bp, corresponding to sequence B (figure shows positions 2411–2433 of SEQ ID NO:1 with the indicated mutation shown at position 2422); and sequence homozygous for a C-G mutation (sequence C) (figures shows positions 2411–2433 of SEQ ID NO:1 with the mutation shown at position 2422).

DESCRIPTION OF PREFERRED EMBODIMENT

The present invention relates to a DNA sequence of the 5' flanking region of the 5-HT1A receptor gene, from about −3438 to about −393 (SEQ ID NO:1), wherein said sequence contains a mutation that results in an inhibition of protein-DNA interactions. The novel DNA sequence can be used as a genetic marker in a diagnostic or prognostic test for mental illnesses that involve the serotonin system. This invention further relates to proteins, which bind to this region and the use of said proteins to develop therapeutics to treat depression and related illnesses that involve the serotonin system. this invention also relates to a glucocorticoid-responsive element located from about −393 to the ATG initiation codon of the 5-HT1A receptor gene.

In the context of the present invention a mutation includes any modification of the DNA sequence. Such modifications include but are not limited to single or multiple base pair changes, inversion, deletions or insertion.

Figure 2:
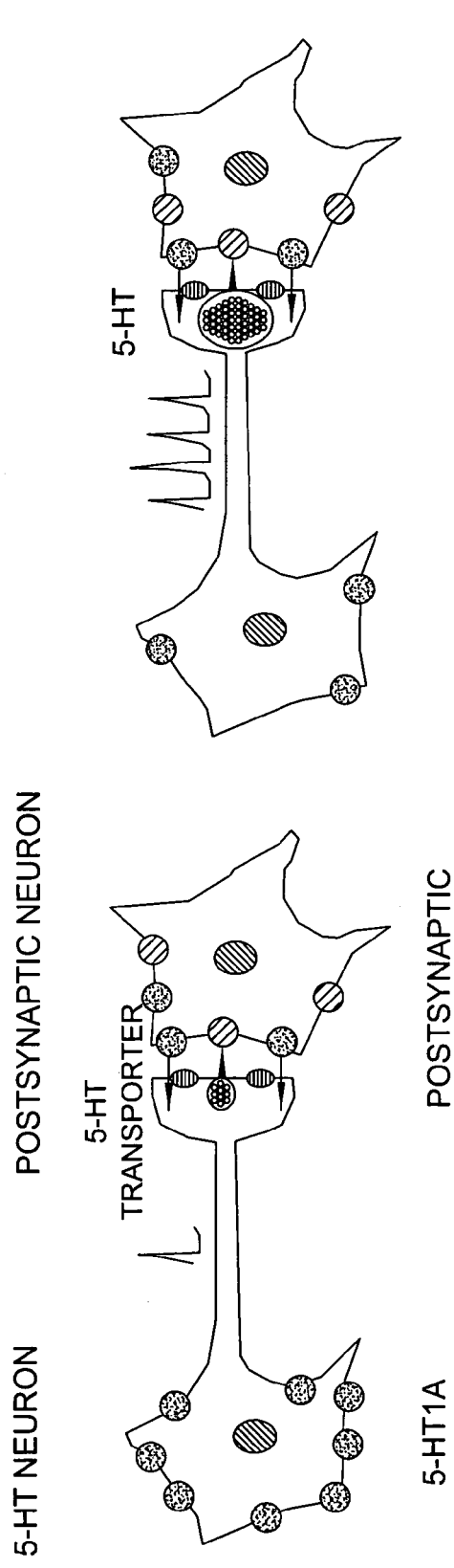
FIG. 2 shows acute and chronic actions of antidepressants on the serotonin system. Acutely, antidepressants that block the presynaptic 5-HT reuptake transporter (eg. SSRIS) inhibit serotonergic firing via recurrent or dendro-dendritic activation of 5-HT1A autoreceptors. After 3 weeks of treatment, a reduction in the number of 5-HT1A autoreceptors via homologous desensitization is observed: this disinhibits the serotonergic neuron, enhancing action potential firing rate, and increasing serotonergic neurotransmission. See text for discussion.
Figure 3:
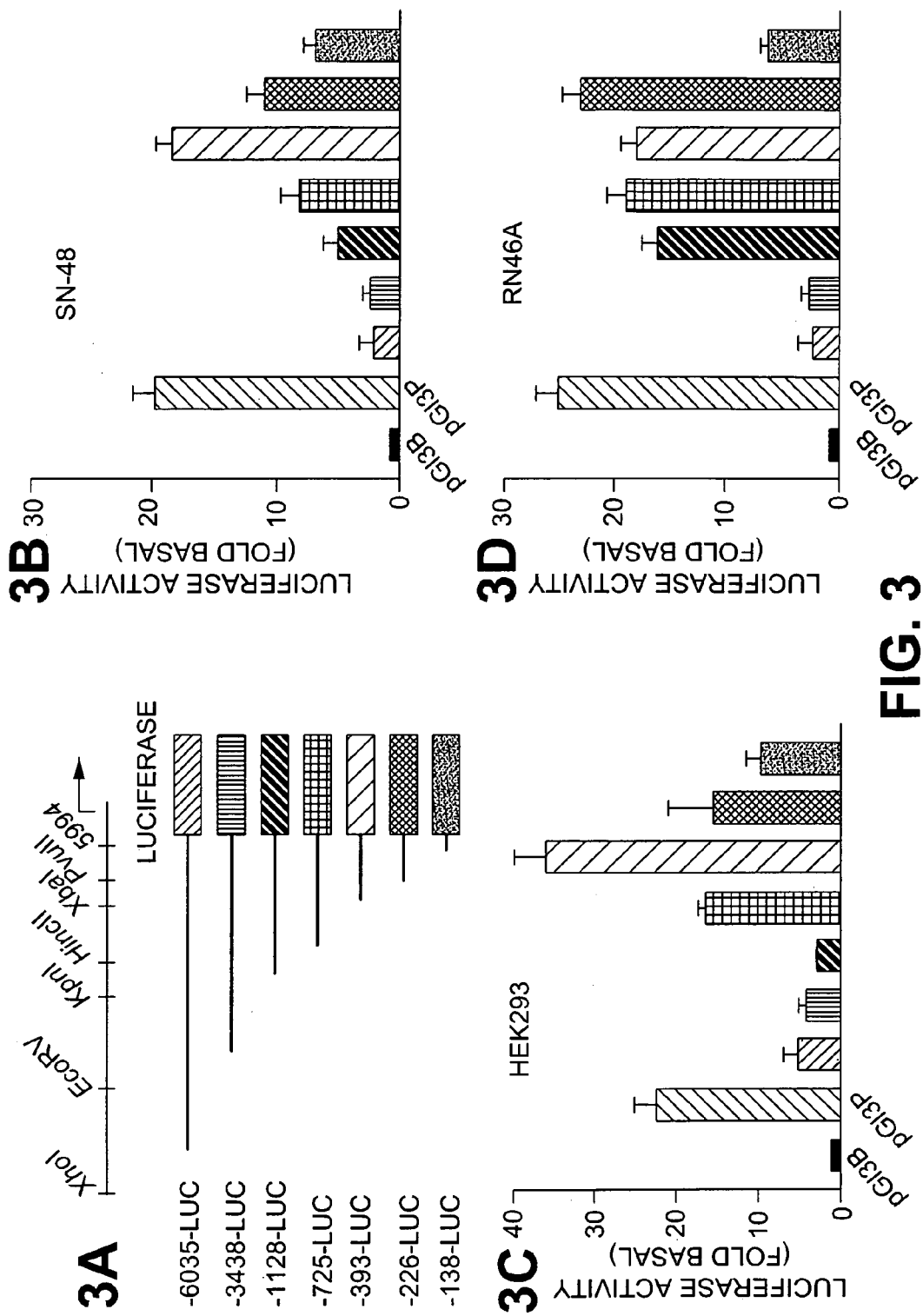
FIG. 3 shows regions of cell-specific transcriptional repressor activity of the 5-HT1A receptor gene. The transcription start site of the human 5-HT1A receptor gene is shown by the solid arrow and restriction sites used to produce the luciferase reporter constructs are indicated as well. Numbers indicate the luciferase reporter constructs are indicated as well. Numbers indicate distance from the initial coding ATG codon. Luciferase activity of each reporter construct is normalized that of basal activity of the vector (pGL3-Basic), with pGL3-Promoter plasmid as a positive control. Activities were obtained from eleven (SN-48), four (HEK-293) or thirteen (RN46A) separate experiments in which triplicate transfections were performed and corrected for transfection efficiency with a co-transfected pCMV-βGal plasmid. Data are presented as mean±SD.

According to the present invention there has been identified a proximal ubiquitous promoter region of the 5-HT1A receptor gene. The promoter region is flanked by a repressor located between −1128 and −393 bp of the ATG codon in SN-48 cells. In RN46A cells repressor activity was located between −3438 and −1128 bp upstream of the ATG codon, suggesting cell-type specific regulation of the 5-HT1A receptor gene. As described above, SSRIs used to treat major depression appear to exhibit clinical effects upon the down-regulation of the 5-HT1A receptor, ie. turning off of the 5-HT1A gene. This suggests that one of the abnormalities that could result in a tendency towards depression would be an elevated basal expression of 5-HT1A receptors. As shown in FIG. 2, an excess of 5-HT1A autoreceptors would depress the firing of the raphe nucleus, reducing the release of 5-HT.

Thus, mutations in the repressor region of the 5-HT1A receptor gene would reduce or disrupt the repressor function leading to enhanced 5-HT1A autoreceptor expression and decreased serotonergic neurotransmission.

In one embodiment of the present invention a C-G change at −1017 bp (position 2422 of SEQ ID NO:1) was identified. According to the present invention, the occurrence of G at −1017 bp was found to correlate with patients with mental illness. In a population of depressed patients 80% were either homozygous or heterozygous for this change; 30% of the patients were homozygous for this change. Prior to the present invention there was no evidence for a clear genetic association with a particular mental illness. From the results of the present invention, the identification of a homozygous C-G polymorphism, which strongly correlated with depressed patients and absent in normals, provides evidence of the use of this polymorphism as a genetic marker for mental illness. Increasingly, PCR-based gene detection is being used in prognostic and diagnostic evaluation of patients, and in criminological identification and characterization. For example, genetic testing of children of affected adults may allow for counseling or early treatment prior to development of an episode of major depression. Furthermore, as data accumulates it may be possible to correlate the genetic change with properties such as severity or drug treatment response.

Thus, according to one aspect of this invention there is provided a DNA sequence containing a mutation in the repressor region of the 5-HT1A receptor gene characterized in that it reduces or disrupts the repressor function leading to enhanced 5-HT1A autoreceptor expression. In one embodiment there is provided a DNA sequence which contains a C-G change at −1017 bp in the repressor region of the 5-HT1A receptor gene. In a further embodiment of the present invention there is provided an imperfect palindromic sequence that flanks the C-G site. The palindrome has the sequence 5'-AA<u>C</u>GAAGACNNNNNNNGTCTTCTT-3' (SEQ ID NO:2) (polymorphic site shown in double underline). The palindrome forms a structure that is recognized by DNA binding proteins.

The DNA sequence described above can be used, according to a further aspect of the present invention, as a diagnostic or prognostic marker for mental illness and behavioral disorders, as well as a predictive marker of behavioral traits. In this aspect of the invention the DNA sequence can be used a probe in a diagnostic or prognostic test. The probe can be of any suitable length, as is well known in the art. A DNA probe ranging in length from about 10 to about 50 nucleic acids would be suitable. The diagnostic or prognostic test could also include PCR amplification of the target sequence in a test sample, which is well know in the art. The primers used in the tests will of course flank the target sequence, one of such primers being for the sense strand and one other of such primers being for the anti-sense strand. An appropriately labeled DNA probe, as describe above could then be used to identify the target sequence in the test sample. The diagnostic or prognostic test could also include the sequencing of the target sequence in the test sample to identify the nucleotide sequence of the target sequence in the test sample.

In one example of this embodiment, the PCR primers were designed to amplify a −718 bp fragment of the human 5-HT1A 5'-flanking region from −1593 to −876 bp of the initial ATG codon. The sense primer had the following sequence: 5'-GTGGCGAACATAAAACCTCA-3' (SEQ ID NO: 3), and the antisense primer had the following sequence: 5'-TTCTTAAATCGTGTCAGCATC-3' (SEQ ID NO: 4).

For a diagnostic kit, primers to amplify a smaller segment (e.g., 100–200 bp) surrounding the polymorphism would be designed and used in PCR of blood samples. The PCR products would then be analyzed by DNA sequence analysis, or by SSCP to probe for the polymorphism. Alternately, if the appropriate restriction enzyme becomes available, digestion with a restriction enzyme that differentiates between normal and polymorphic sequences could be used for the analysis of the PCR product. These assays would identify normal, heterozygous and homozygous alleles. Alternately, the repressor protein or specific antibodies that bind to the polymorphic site could be developed for use as an ELISA or radio-receptor competition assay for the present of the polymorphism. Although rapid and efficient the competition binding assays may not be sensitive enough to discriminate between heterozygous and homozygous polymorphisms.

In the context of the present invention the target sequence in the test sample will include the mutation in the repressor region of the 5-HT1A receptor gene. In one aspect of the invention the target sequence will include the −1017 bp locus.

The present invention further includes within its scope kits for the identification of the mutation, deletion or insertion in the repressor region of the 5-HT1A receptor gene. The kits will include a DNA sequence, as described above, to be used as a probe, together with other reagents required to complete the diagnostic or prognostic test. These reagents include but are not limited to DNA primers for PCR amplification of the target sequence together with reagents and enzymes required for PCR.

As SSRIs are effective not only in treatment of major depression, but also of related mental illnesses that involve the serotonin system, such as bipolar depression, generalized anxiety disorder, obsessive-compulsive disorder, and panic disorder. Agents that directly modify the 5-HT1A receptor, such as agonists like buspirone, are effective in the treatment of generalized anxiety, and are beginning to be used for treatment of the negative symptoms of schizophrenia. Finally, agents that release serotonin (d-fenfluramine) are effective in eating disorders. One component of these illnesses could be abnormal regulation of the 5-HT1A receptor due to the polymorphic change at −1017 bp. Thus the identification of this polymorphism can provide a marker for sub-dividing the severity, phenotype, or treatment responsiveness of patients with these diseases.

Consistent with a functional role for the −1017 bp polymorphic region in regulation of the 5-HT1A gene, the present invention further comprises a protein complex from raphe nuclei that interacts with a 31-bp segment in this region. The 31-bp segment contains both the polymorphic site and a palindromic DNA sequence.

According to the present invention, the polymorphic site is in a region that has repressor activity in raphe cells, and the C-G mutation reduces this activity by inhibiting protein-DNA interactions. This leads to an enhanced expression of the 5-HT1A autoreceptor, which contributes to a greater predisposition towards major depression. Thus the protein or proteins that bind to the polymorphic region function as repressors of the 5-HT1A receptor, and constitute important drug targets for the development of novel therapeutic compounds to treat depression and related illnesses.

Thus according to this aspect of the present invention the "wild type" region is used to identify proteins that bind to the repressor region. These naturally occurring proteins could then be modified so as to improve the protein-DNA interactions in the mutated repressor, to thus mimic the normal binding.

In addition, novel therapeutics, based on improving the protein-DNA binding could be identified using the mutated repressor region of the present invention. Thus this invention is also directed to a method of identifying novel therapeutics using a DNA sequence containing a mutation in the repressor region of the 5-HT1A receptor gene, to identify therapeutics that have an improved protein-DNA binding capability with the mutated repressor. Novel therapeutics that act to enhance the expression or activity of the repressor protein would also be covered by the present invention.

Novel therapeutics could be identified using a number of known techniques. For example an oligonucleotide incorporating the repressor DNA element could be used to screen a cDNA expression library and clone cDNA's of proteins that bind to the oligonucleotide in a specific manner. Also an oligonucleotide incorporating the repressor DNA element cloned opposite a reporter gene could be used to screen a cDNA library fused to the appropriate activation domain for the reporter gene in yeast or mammalian one-hybrid approach. Alternatively the repressor element could be used to generate reagents for the purification of the binding proteins that interact with that element. The repressor element could also be used as a probe to follow the purification of proteins that interact with the element.

The DNA sequences of the present invention can also be used to develop mimetics of the DNA binding domain of the repressor that can inhibit competitively the activity of proteins that bind to the repressor region in cases where it is important to reduce the DNA-protein interaction (eg., in hyper-aggressive patients). Alternately, the DNA sequence could be used to develop oligonucleotide analogous of the binding site to squelch the activity of proteins that bind to the repressor region. In addition, novel therapeutics that reduce the expression or activity of the repressor protein would also be covered by the invention.

As previously discussed, within the proximal 5'-flanking region of the human 5-HT1A receptor a novel glucocorticoid responsive region that suppresses reporter gene expression has been identified. In SN-48 cells, a model of post-synaptic 5-HT1A expressing neuron, dexamethasone pretreatment suppresses the expression of the 5-HT1A receptor gene by acting at a glucocorticoid-responsive element located from between −393 bp and the ATG initiation codon, and more specifically from about −226 bp to about −138 bp from the initial ATG codon. This element differs from previously-described GRE sequences and thus represents a novel glucocorticoid element.

The glucocorticoid-mediated repression of the 5-HT1A receptor is another mechanism by which the expression of the receptor may be regulated. For example, a large proportion of depressed patients have attenuated response to dexamethasone suppression, symptomatic of reduced glucocorticoid responsiveness and leading to elevated levels of glucocorticoids. Alteration in the DNA sequence that mediates glucocorticoid regulation could lead to abnormal over-expression of the 5-HT1A receptor. Such alteration in the glucocorticoid response region of the 5-HT1A gene may be prognostic of patients that respond to glucocorticoid therapy in combination with anti-depressant compounds.

The present invention is illustrated in the following examples, which are not to be construed as limiting.

EXAMPLES

Methods

Construction of Luciferase Reporters

The luciferase plasmid −6035-luc was obtained by subcloning the 5'-flanking SalI/BssHII 6-Kb fragment of the human 5-HT1A receptor gene into the XhoI/MluI site of a modified pGL3-Basic vector (Promega) containing a repeated KpnI/SmaI cassette in the reverse orientation. From −6035-luc, all subsequent constructs were generated. The −3438-luc and −226-luc were constructed by digestion with EcoRV and PvuII respectively, followed by internal ligation. The −1128-luc was obtained by insertion of a KpnI/BssHII fragment into pGL3-Basic vector (Promega) digested with KpnI and MluI. Digestion with HincII and SmaI generated a fragment that was inserted into the SmaI site of pGL3-Basic to produce −725-luc construct. Similarly, the DNA segment obtained by digestion with XbaI and NheI was inserted into the NheI site of pGL3-Basic and was called −393-luc. Finally, PCR amplification of a proximal 164-bp fragment gave a product that was then digested with HindIII and subcloned into a SmaI and HindIII digested pGL3-Basic vector to generate −138-luc. All plasmids were purified by CsCl equilibrium gradient centrifugation and quantified spectrophotometrically (Ausubel et al., 1989).

Cell Lines and Transient Transfections

Mouse septal-neuroblastoma SN-48 cells and human embryonic kidney cells HEK-293 were grown in Dulbecco's modified Eagle medium (DMEM) (Gibco BRL) supplemented with 10% v/v heat-inactivated fetal bovine serum (FBS) at 37° C. in 5% $CO_2$. SN-48 cells were differentiated by reduction of FBS to 1% v/v and treatment with 10 µM retinoic acid. The rat raphe RN46A cells were cultured in Neurobasal medium (Gibco BRL) supplemented with 10% v/v heat-inactivated FBS and 0.5 mM 1-glutamine at 33° C. in 5% $CO_2$.

SN-48 and HEK-293 cells were transfected in 10 cm dishes using the calcium phosphate co-precipitation method (Ausubel et al., 1989). To correct for differences in transfections efficiencies between dishes, 2 µg of pCMV-βgal plasmid were co-transfected with 20 µg of luciferase reporter constructs. After 14–16 hours incubation with $CaHPO_4$, cells were passage into three 3.5 cm dishes, and incubated for 36 hours with fresh medium containing penicillin (50 U/ml) and streptomycin (50 µg/ml) before assaying for luciferase activity. SN-48 cells were differentiated during this period of time and if applicable, treated 12 hours prior to harvest with 10 nM aldosterone and 1 µM dexamethasone in DMEM supplemented with 1% heat-inactivated charcoal-treated serum.

RN46A cells were transfected in 3.5-cm Primaria dishes (Falcon) using Pfx-7 (Invitrogen) lipid mixture according to manufacturers recommendations. Cells were transfected with 0.5 µg pCMV-βgal, 1.5 µg luciferase plasmid and 12 µg Pfx-7 (6:1 lipid to DNA ratio) using serum-free medium Neurobasal medium. Cells were transfected overnight and fed the next day with complete Neurobasal medium for 24 hours. When applicable, cells were treated during this period of time with 10 nM aldosterone and 1 µM dexamethasone in Neurobasal medium supplemented with 10% dialyzed serum.

Luciferase and MUG Assays

Cells were washed once with PBS and lysed in 200 µl of Reporter Lysis Buffer (Promega) and collected by scraping. After one freeze-thaw cycle, luciferase activity in the lysate was determined using a BioOrbit 1250 luminometer. β-galactosidase activity was determined in the same samples using MUG substrate and Z-buffer (Ausubel et al., 1989). Luciferase activity was divided by β-galactosidase activity to normalize for transfection efficiency. These values were then normalized to the activity of the vector (pGL3-Basic) All experiments were repeated at least 3 times and compared to positive pGL3-Promoter, Promega) and negative (pGL3-Basic, Promega) controls.

PCR Amplification of 5-HT1A Receptor 5'-Flanking Region from Blood Samples and Sequencing Blood samples from depressed patients were collected following extensive characterization of the patients for clinical drug trial. Documentation of the patients tested is included in Appendix 1. DNA samples from a random pool of normal individuals were also collected. The blood samples were either amplified directly or subjected to DNA extraction before amplification using optimal PCR conditions and primers. DNA extraction from whole blood samples was done using the Split Second DNA Preparation Kit (Boehringer Mannheim). When used directly, diluted blood samples were, prior to PCR amplification, subjected to three heat and cool cycles at 95° C. and 55° C. PCR primers were designed to amplify a −718 bp fragment of the human 5-TH1A 5'-flanking region from −1593 to −876 bp of the initial ATG codon. The sense primer had the following sequence: 5'-GTGGCGAACATAAAACCTCA-3' (SEQ ID NO:3), and the antisense primer had the following sequence: 5'-TTCTTAAATCGTGTCAGCATC-3' (SEQ ID NO:4). PCR products were electrophoresed on a 1.0% agarose gel and DNA bands were purified, free of oligonucleotide primers, using the QIAEX II Gel Extraction Kit (Qiagen). Purified DNA was then heat-denatured at 95° C. and snap-cooled in an ethanol/dry ice bath followed by a 30-min. annealing with PCR primers. Preparation was then sequenced using the Sanger dideoxy termination method (T7 sequencing kit, Pharmacia biotech).

Nuclear Extract Preparation

RN46A cells ($10^7$) were washed once with PBS and harvested in 100 μl of buffer A (10 mM Tris pH 8.0, 1.5 mM $MgCl_2$, 5 mM KCl, 0.5 mM DTT, 0.5 mM PMSF, 0.5% NP-40). Cells were incubated on ice for 10 min. and spun at 500×g at 4° C. for 15 min. The nuclear pellet was resuspended in 30 μl of buffer B (20 mM Tris pH 8.0, 25% glycerol, 1.5 mM $MgCl_2$, 0.5 mM PMSF, 0.2 mM EDTA, 0.5 mM DTT, 0.4 mM NaCl), stirred gently and incubated on ice for 15 min. Nuclear debris was then pelleted by a final centrifugation stage of 8,000×g, 4° C., 30 min. The supernatant was transferred to a clean microfuge tube and stored at −80° C. until required. Protein levels in nuclear extracts were determined using the bicinchonic protein assay (BCA) from Pierce.

Electrophoretic Mobility Shift Assay

Probe and respective competitors were made by annealing synthesized complementary oligodeoxynucleotides from the normal human 5-HT1A sequence: sense −1024/−996 bp 5'-TTAAAAACGAAGACACACTCGGTCTTCTT-3' (SEQ ID NO: 5); antisense −994/−1022 bp 5'-GGAAGAAGAC-CGAGTGTGTCTTCG TTTTT-3' (SEQ ID NO: 6) containing the polymorphic site (in double underline) and palindromic sequence used as a probe in the mobility shift assay, and the rat 5-HT1A sequence 5'-CGGCATAAGCAAGC-CCTTATTGCACAGAGCT-3' (SEQ ID NO: 7) was used as a non-specific competitor. The probe 5' overhangs were filled-in with 100uCi of α[$^{32}$P] dCTP using 2.5 U of Klenow fragment DNA polymerase to generate a 31-bp labeled double-stranded DNA probe. Unincorporated radioactivity was removed by chromatography over a Sephadex G-50 column and the specific activity of the probe was determined. Labeled probe (60 000 cpm/sample) was incubated on ice with 15 μg of nuclear protein extract in binding buffer (20 mM Hepes, 0.2 mM EDTA, 0.2 mM EGTA, 100 mM KCl, 5% glycerol, 2 mM DTT) for 20 min. Samples were electrophoresed on a 5% acrylamide/Tris-glycine gel at 4° C. for 3 hours.

Results

We have investigated the promoter/enhancer activities of the human 5-HT1A receptor gene using a series of luciferase reporter constructs including over 6 Kb of 5 flanking sequence. These constructs were transiently transfected into various cell lines expressing (rat raphe RN46A, mouse septal SN-48) or not (HEK 293) endogenous 5-HT1A receptors. The SN-48 cells are derived from septal neurons (Charest et al., 1993; Lee et al., 1991), providing a model for the regulation of the 5-HT1A receptor gene in of post-synaptic (non-serotonergic) neurons. By contrast the RN46A cells are derived from serotonergic cells of the raphe nuclei (Eaton et al., 1995) and provide a model of presynaptic regulation of the 5-HT1A receptor. The HEK-293 cells which do not express the 5-HT1A receptor serve as a negative control to examine non-selective DNA elements in the 5-HT1A receptor gene that are capable of driving expression regardless of whether the cell normally expresses the receptor.

Basal Regulation of the Human 5-HT1A Receptor Gene

In each cell line, the luciferase activity of extracts from transfected cells reached a maximal level of 20-to 30-fold basal with the −393-luc construct. This indicates that DNA elements located within the first 393 bp possess a non-selective promoter activity that is equally active regardless of whether the receptor is normally expressed in those cells. Cell-specific activity occurred in the large constructs that repressed the promoter activity. In particular, the −1128-luc construct had very low activity in HEK-293 cells, intermediate activity in SN-48 cells, and full activity in RN46A cells. However, the addition of further 5' sequences led to low activity in all cell types (ie. in the −3438-luc and −6035-luc constructs). These results indicate that in HEK 293 cells that do not express endogenous 5-HT1A receptors, a proximal 393-bp promoter region is flanked by repressor elements located between −1128 and −393 of the initial ATG codon. Note that in HEK 293 cells, this repressor region is more active than in receptor-positive SN-48 cells. In SN-48, transiently transfected with human 5-HT1A promoter constructs, a proximal −393 bp promoter region that is progressively repressed by DNA elements located between −3438 and −393 bp of the initial ATG codon. In RN46A cells, the repressor activity is located further upstream between −3438 and −1128 bp of the ATG codon suggesting a cell-type specific regulation of the human 5-HT1A receptor gene by elements between −3438 and −393 bp.

Glucocorticoid-Mediated Regulation of the 5-HT1A Gene

Figure 4A:
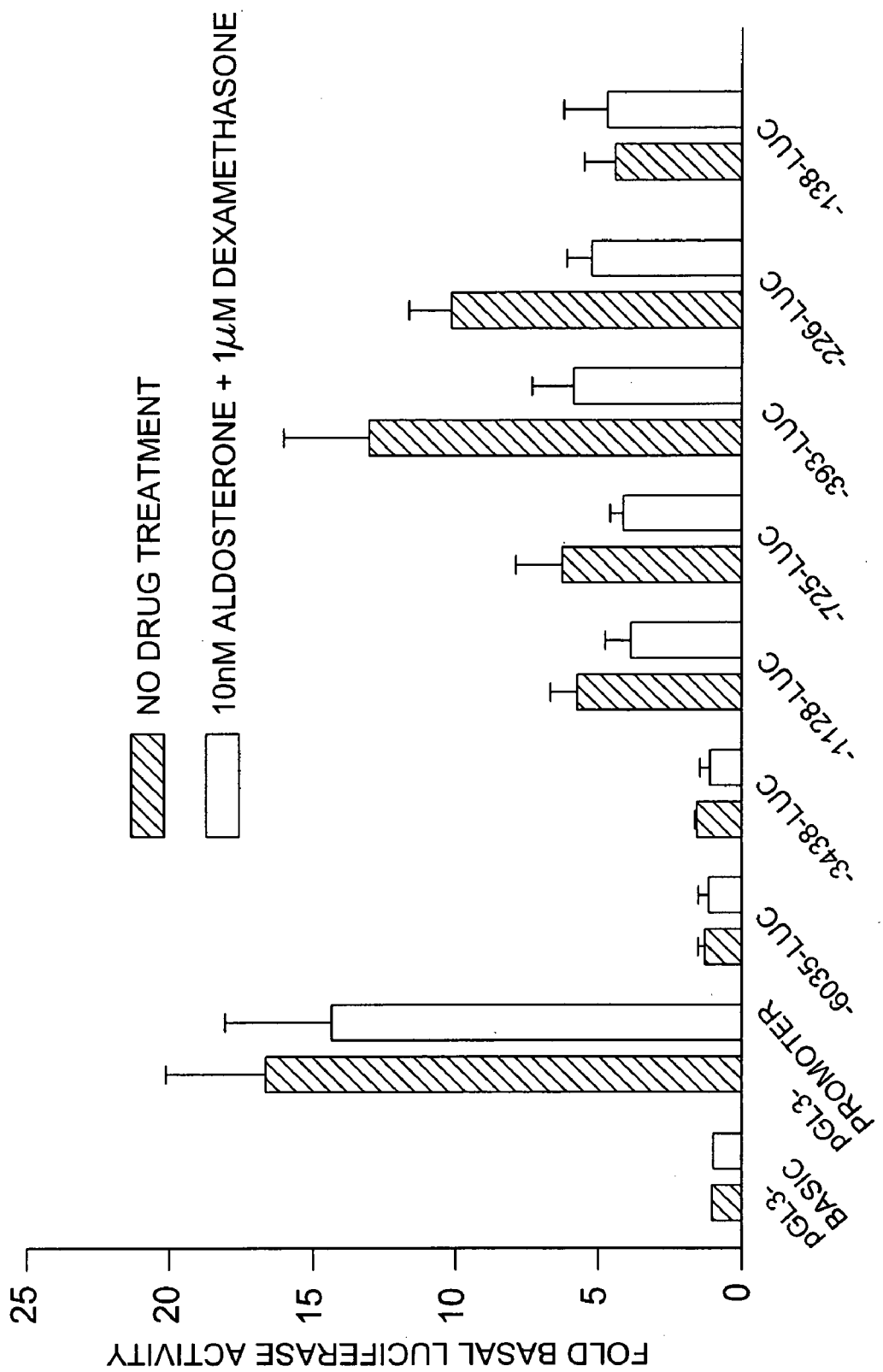
FIG. 4 shows glucocorticoid-induced suppression of 5-HT1A gene in SN-48 (FIG. 4a) cells, but not RN46A (FIG. 4b) cells. Numbers indicate distance from the initial ATG codon (see FIG. 3). Luciferase activity of each reporter construct is normalize to that of the vector (pGL3-Basic). Activities were obtained from thirteen separate experiments in which triplicate transfections were performed and corrected for transfection efficiency with a co-transfected pCMV-βGal plasmid. Error bars indicate mean±SD, n=13.
Figure 4B:
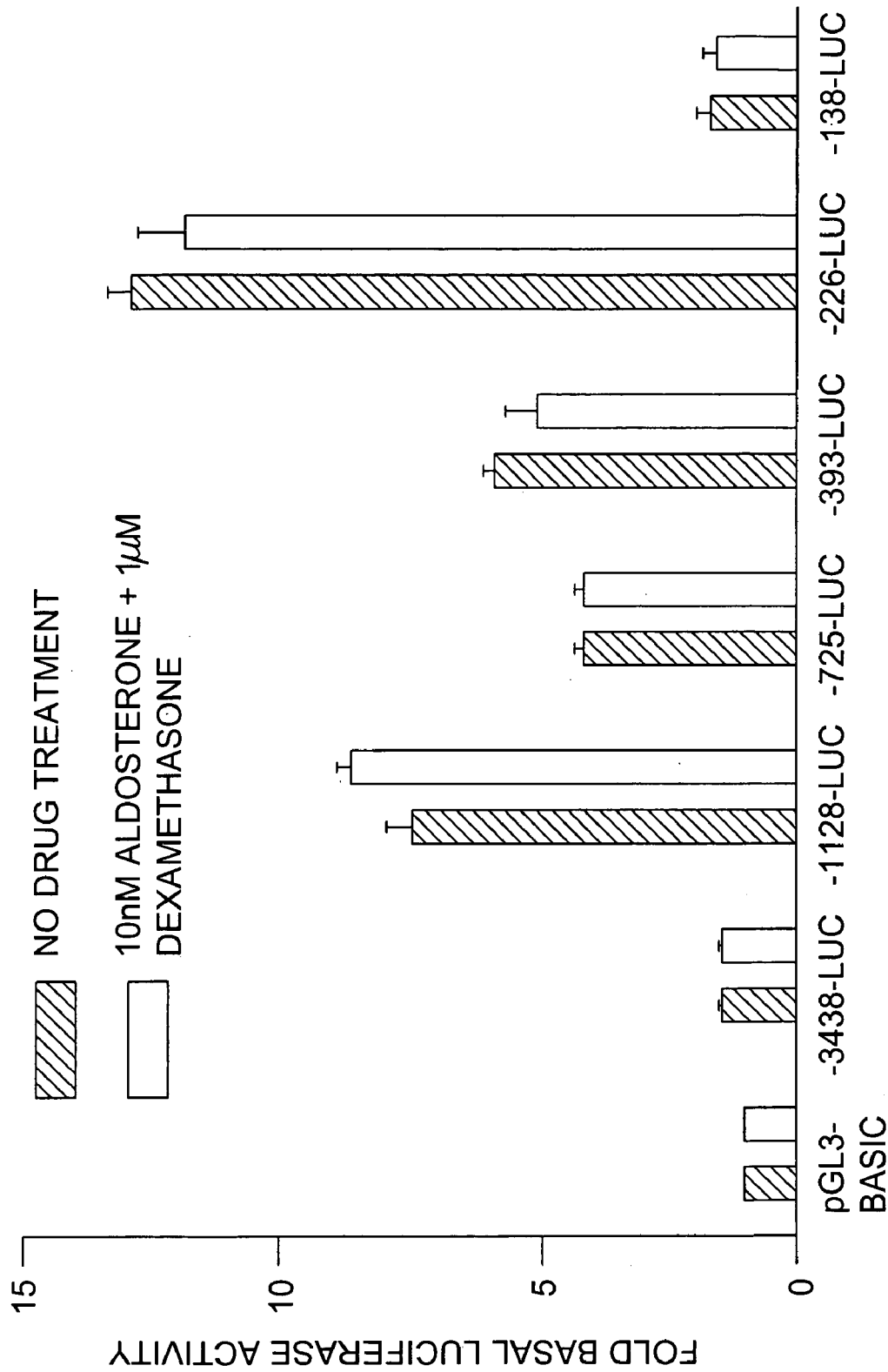

Another mode of transcriptional repression of the 5-HT1A receptor gene is the negative regulation by glucocorticoids, especially in post-synaptic tissues like hippocampus. We investigated whether glucocorticoids mediated gene repression by measuring the activity of 5-HT1A-luciferase reporter constructs in the absence or presence of glucocorticoid treatment. In differentiated SN-48 cells, a model of post synaptic 5-HT1A expressing neurons, treatment for 12 hours with 10 nM aldosterone and 1 μM dexamethasone suppressed the transcription of the 5-HT1A receptor gene in all active constructs except the −138-luc transfection (FIG. 4a). In the largest 5-HT1A constructs (−6035-luc and −3438-luc) the activity was too weak to detect glucocorticoid-induced suppression. Glucocorticoid-mediated suppression was promoter-specific, since the activity of the pGL3-Promoter transfection was not altered by glucocorticoid treatment. By contrast, in RN46A cells, a model of presynaptic serotonergic neurons, treatment with aldosterone/dexamethasone for 24 hours had no effect on the ability of the proximal 5'-flanking sequence of the human 5-HT1A receptor to drive transcription of the luciferase reporter gene (FIG. 4b). These data indicate that glucocorticoids mediate suppression in post-synaptic model SN-48 cells by acting at a glucocorticoid-responsive element located between −226 and−138 bp of the initial ATG codon. This region is clearly distinct from the upstream regions between −3438 and −393 bp that mediate cell-specific repression of the basal expression of the 5-HT1A receptor gene.

5-HT1A Receptor Gene Polymorphism in Depressed Patients

Figure 5:
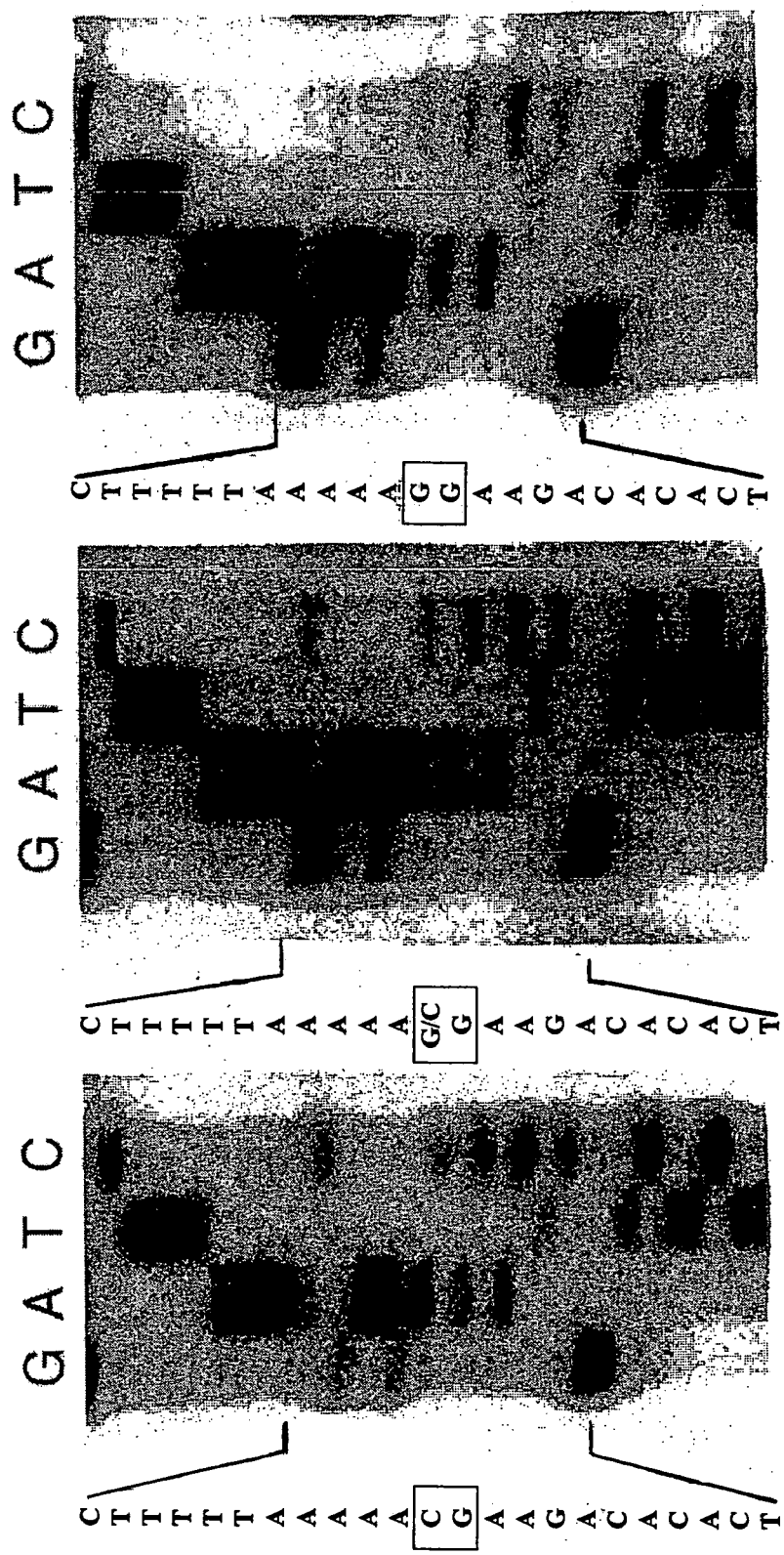
FIG. 5 shows the detection of the C-G polymorphism at −1017 bp of the 5-HT1A gene in human blood samples.

A repressive region of the 5-HT1A promoter from −1593 to −876 bp of the initiator ATG codon was analyzed for variation in size or sequence that could alter the basal expression of the 5-HT1A receptor gene or receptor down-regulation in response to antidepressant agents. To do so, blood samples from depressed and normal patients were amplified in this region of the 5-HT1A receptor gene by PCR and sequenced. The use of a direct sequencing protocol allowed the determination of homozygosity or heterozygosity (FIG. 5). Using this protocol we detected only a single site of nucleotide alteration of C-G that was located at −1017 bp from the initiator ATG. As summarized for 43 patients analyzed to date in Table I, a large proportion (80%) of patients were either heterozygous or homozygous for this change; 30% of the patients were homozygous for the C-G change. In contrast, randomly-selected normals were about 50% heterozygous, and none of the normals was homozygous for the C-G transition. Thus the homozygous C-G(−1017) change is strictly associated with depressed patients.

TABLE 1

Distribution of 5-HT1A receptor gene polymorphism C-G (−1017 bp) among normals and depressed patients.
Genomic DNA from blood samples of normals or depressed patients was amplified and sequenced to determine the presence of the C/G polymorphism located at 1017 of the 5-HT1A receptor gene. The distribution of wild-type (+/+), heterozygous (+/0) and homozygous (0/0) polymorphisms is tabulated as number of samples with % of total in parentheses.

| Phenotype | Genotype | | |
|---|---|---|---|
| | +/+ | +/0 | 0/0 |
| Normal | 11 (48%) | 12 (52%) | 0 (0%) |
| Depressed | 9 (21%) | 21 (49%) | 13 (30%) |

Protein Interactions at the Polymorphic Site

Figure 6:
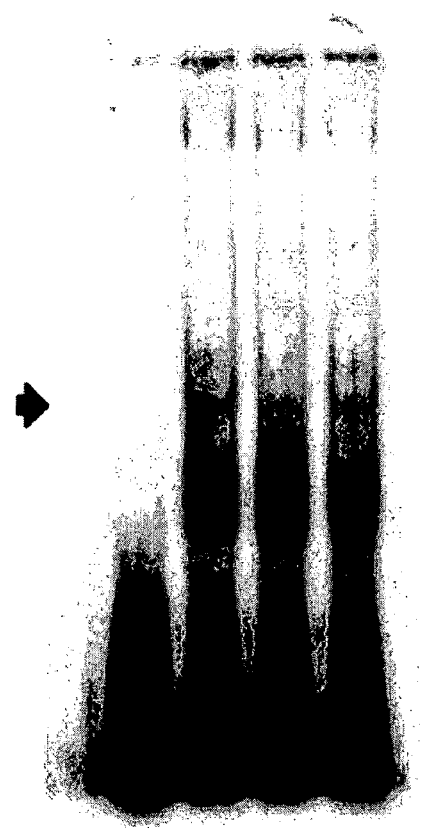
FIG. 6 shows the association of nuclear proteins with the polymorphic site of the 5-HT1A receptor gene. Gel mobility shift assay was done using nuclear extracts prepared from RN46A cells. The specific 31-bp probe spans the palindrome where the polymorphic point mutation in depressed patients has been found at −1017 bp (position 2422 of SEQ ID NO:1) from the initial ATG codon of the human 5-HT1A promoter sequence, and was present in all samples. Nuclear extract, 100-fold molar excess of unlabeled specific 31-bp oligonucleotide of unrelated sequence were added to the incubation as indicated. A specific shifted complex is indicated by the arrowhead.

The identification of a polymorphic change that correlates with major depression raises the important question of whether the −1017 bp region has functional activity. This region participates in the cell-specific basal repression of the 5-HT1A receptor gene based on its general location. Functional activity is demonstrated by the presence of a complex in nuclear protein extracts that binds specifically to a 31-bp region flanking −1017 bp (FIG. 6). As detected by gel mobility shift assay, in the presence of nuclear extract from raphe RN46A cells several complexes were detected compared to without extract (lane 1). However, only the complex indicated was susceptible to competition with unlabeled specific 31-bp oligonucleotide, but not by an unrelated oligonucleotide, indicating a specific interaction. The other complexes may represent high capacity/low affinity interactions with the poly-A repeat segment of the 31-bp oligonucleotide. Thus, RN46A cells contain a specific nuclear complex that interacts with the −1017-bp region of the 5-HT1A receptor. Within the sequence flanking the C-G site (double-underlined) is a palindrome indicated in bold 5'-AACGAAGACNNNNNNNGTCTTCTT-3' (SEQ ID NO:2). The palindrome forms a structure that is recognized by DNA binding proteins. For example, steroid receptors recognize palindromic sequences as specific DNA binding sites (Evans, 1988). The C-G mutation may alter the stability of protein-DNA interactions at this site resulting in a change in 5-HT1A receptor expression or regulation.

REFERENCES

Albert, P. R., P. Lembo, J. M. Storring, A. Charest, and C. Saucier. 1996. The 5-HT1A receptor: signaling, desensitization, and gene transcription [see comments]. *Neuropsychopharmacology.* 14:19–25.

Ausubel, F. M., R. Brent, R. E. Kingston, D. D. Moore, J. G. Smith, J. G. Siedman, and K. Struhl. 1989. Current protocols in molecular biology. John Wiley and Sons, New York.

Blier, P., d. M. C., and Y. Chaput. 1990. A role for the serotonin system in the mechanism of action of antidepressant treatments: preclinical evidence. [Review]. *J. Clin. Psychiat.*

Blier, P., and C. de Montigny. 1994. Current advances and trends in the treatment of depression [see comments]. [Review]. *Trends Pharmacol. Sci.* 15:220–226.

Charest, A., B. H. Wainer, and P. R. Albert. 1993. Cloning and differentiation-induced expression of a murine serotonin1A receptor in a septal cell line. *J. Neurosci.* 13:5164–5171.

Charney, D. S., J. H. Krystal, P. L. Delgado, and G. R. Heninger. 1990. Serotonin-specific drugs for anxiety and depressive disorders. *Annu. Rev. Med.* 41:437–446.

Eaton, M. J., J. K. Staley, M. Y. Globus, and S. R. Whittemore. 1995. Developmental regulation of early serotonergic neuronal differentiation: the role of brain-derived neurotrophic factor and membrane depolarization. *Dev. Biol.* 170:169–182.

Evans, R. M. 1988. The steroid and thyroid hormone receptor superfamily. *Science.* 240:889–895.

Fanelli, R. J., and K. McMonagle-Strucko. 1992. Alteration of 5-HT1A receptor binding sites following chronic treatment with ipsapirone measured by quantitative autoradiography. *Synapse.* 12:75–81.

Hoyer, D., D. E. Clarke, J. R. Fozard, P. R. Hartig, G. R. Martin, E. J. Mylecharane, P. R. Saxena, and P. P. Humphrey. 1994. International Union of Pharmacology classification of receptors for 5-hydroxytryptamine (Serotonin). [Review]. *Pharmacol. Rev.* 46:157–203.

Jacobs, B. L., and E. C. Azmitia. 1992. Structure and function of the brain serotonin system. *Physiological Reviews.* 72:165–229.

Lee, H. J., G. J. Elliot, D. N. Hammond, V. M. Lee, and B. H. Wainer. 1991. Constitutive expression of the mature array of neurofilament proteins by a CNS neuronal cell line. *Brain Res.* 558:197–208.

Mongeau, R., P. Blier, and C. de Montigny. 1997. The serotonergic and noradrenergic systems of the hippocampus: their interactions and the effects of antidepressant treatments. *Brain Res. Rev.* 23:145–195.

Mongeau, R., S. A. Welner, R. Quirion, and B. E. Suranyi-Cadotte. 1992. Further evidence for differential affinity states of the serotonin1A receptor in rat hippocampus. *Brain Res.* 590:229–238.

Parks, C. L. and T. Shenk. 1996. The serotonin1a receptor gene contains a TATA-less promoter that responds to MAZ and Sp1. *J. Biol. Chem.* 271–4417–4430.

Penington, N. J., and J. S. Kelly. 1990. Serotonin receptor activation reduces calcium current in an acutely dissociated adult central neuron. *Neuron.* 4:751–758.

Penington, N. J., J. S. Kelly, and A. P. Fox. 1993. Whole-cell recordings of inwardly rectifying K+ currents activated by 5-HT1A receptors on dorsal raphe neurones of the adult rat. *J. Physiol.* 469:387–405.

Schoenherr, C. J., and D. J. Anderson. 1995. Silencing is golden: negative regulation in the control of neuronal gene transcription. *Curr. Opin. Neurobiol.* 5:566–571.

Tork, I. 1990. Anatomy of the serotonergic system. *Ann. N.Y. Acad. Sci.* 600:9–34; discussion 34–35.

Welner, S. A., C. De Montigny, J. Desroches, P. Desjardins, and B. E. Suranyi-Cadotte. 1989. Autoradiographic quantification of serotonin1A receptors in rat brain following antidepressant drug treatment. *Synapse.* 4:347–352.

Zgombick, J. M., S. G. Beck, C. D. Mahle, B. Craddock-Royal, and S. Maayani. 1989. Pertussis toxin-sensitive guanine nucleotide-binding protein(S) couple adenosine A1 and 5-hydroxytryptamine1A receptors to the same effector systems in rat hippocampus: biochemical and electrophysiological studies. *Mol. Pharmacol.* 35:484–494.

All scientific publications are incorporated herein by reference.

The present invention has been described with regard to preferred embodiment. However, it will be understood to persons skilled in the art that a number of variations and modifications can be made without departing from the scope of the invention as described in the following claims.

The embodiments of the invention in which an exclusive property of privilege is claimed are defined as follows:

1. An isolated DNA molecule consisting of a nucleotide sequence selected from the group consisting of:
   a) a sequence consisting of SEQ ID NO:1 and a C-G substitution mutation at position 2422 of SEQ ID NO:1, wherein said mutation results in a reduction in 5-HT1A receptor repressor function leading to enhanced 5-HT1A receptor expression;
   b) a fragment of said sequence of (a) that is at least 10 nucleotides in length and contains the mutation at position 2422 of SEQ ID NO:1; and
   c) a sequence that is fully complementary to the sequence of (a) or (b).

2. The isolated DNA molecule of claim 1, wherein the fragment of (b) is between about 10 and about 50 nucleotides in length and contains the mutation at position 2422 of SEQ ID NO:1.

3. The isolated DNA molecule of claim 1, wherein the isolated DNA molecule consists of SEQ ID NO:1 and the C-G substitution mutation at position 2422 of SEQ ID NO:1, wherein the mutation results in a reduction in 5-HT1A receptor repressor function leading to enhanced 5-HT1A receptor expression.

4. The isolated DNA molecule of claim 1, wherein said fragment of said sequence of (a) comprises positions 2420 to 2443 of SEQ ID NO:1 and said C-G substitution mutation at position 2422 of SEQ ID NO:1.

5. An isolated DNA molecule consisting of the nucleotide sequence of SEQ ID NO:2, or a fragment thereof that is at least 10 nucleotides in length and contains position 3 of SEQ ID NO:2, or a sequence that is fully complementary to SEQ ID NO:2 or said fragment thereof, wherein the DNA molecule forms a structure that is recognized by DNA binding proteins.

6. The isolated DNA molecule of claim 5, consisting of SEQ ID NO:2.

* * * * *